US008084227B2

(12) United States Patent
Yokozeki et al.

(10) Patent No.: US 8,084,227 B2
(45) Date of Patent: Dec. 27, 2011

(54) METHOD FOR PRODUCING DIPEPTIDES

(75) Inventors: Kenzo Yokozeki, Kanagawa (JP); Isao Abe, Kanagawa (JP); Seiichi Hara, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 955 days.

(21) Appl. No.: 11/330,076

(22) Filed: Jan. 12, 2006

(65) Prior Publication Data

US 2006/0177893 A1 Aug. 10, 2006

Related U.S. Application Data

(63) Continuation of application No. PCT/JP2004/010990, filed on Jul. 26, 2004.

(30) Foreign Application Priority Data

Jul. 25, 2003 (JP) .................................. 2003-201820

(51) Int. Cl.
*C12P 21/06* (2006.01)
*C12P 1/00* (2006.01)
*C12N 9/00* (2006.01)
*C12N 9/10* (2006.01)

(52) U.S. Cl. .......... 435/68.1; 435/41; 435/183; 435/193
(58) Field of Classification Search .................. 435/68.1, 435/41
See application file for complete search history.

(56) References Cited

U.S. PATENT DOCUMENTS

| 4,165,311 | A | 8/1979 | Isowa et al. |
| 4,256,836 | A | 3/1981 | Isowa et al. |
| 4,436,925 | A | 3/1984 | Isowa et al. |
| 7,115,389 | B2 | 10/2006 | Hara et al. |
| 2004/0137558 | A1* | 7/2004 | Yokozeki et al. ............ 435/68.1 |
| 2005/0019864 | A1 | 1/2005 | Hara et al. |
| 2005/0124035 | A1 | 6/2005 | Yokozeki et al. |
| 2007/0190602 | A1 | 8/2007 | Abe et al. |

FOREIGN PATENT DOCUMENTS

| EP | 0 278 787 | 8/1988 |
| EP | 1 411 116 | 4/2004 |
| JP | 53-092729 | 8/1978 |
| JP | 01-096194 | 4/1989 |
| JP | 01-502158 | 8/1989 |
| JP | 06-234715 | 8/1994 |
| WO | WO 88/06187 | 8/1988 |
| WO | 90/01555 | 2/1990 |
| WO | WO 03/010307 | 2/2003 |
| WO | WO/03/010189 | * 6/2003 |

OTHER PUBLICATIONS

NCBI (National Center for Biotechnology Information), Taxonomy browser (Pedobacter heparinus), [Retrieved on Jan. 29, 2008]. Retrieved from Internet: <http://www.ncbi.nlm.nih.gov/Taxonomy/Browser/wwwtax.cgi?lvl=0&id=984>.*
Durham, DH, 1990, Applied and Envronmental Microbiology, 56, 2277-2281.*
Furst, P, et al., 1997, Nutrition, 13, 731-737.*
Steyn, PL, et al., 1998, International Journal of Systematic Bacteriology, 48, 165-177.*
A. Sugihara, et al., "A Novel α-Amino-Acid Esterase from *Bacillus mycoides* Capable of Forming Peptides of DD- and DL-Configurations", J. Biochem., vol. 130, 2001, pp. 119-126.
Helle MEOS, et al.. Single-step Synthesis of Kyotorphin in Frozen Solutions by Chymotrypsin. Tetrahedron: Asymmetry, 1993, 4(7), pp. 1559-1564.
Vello Tougu, et al., Peptide Synthesis by Chymotrypsin in Frozen Solutions. Free Amino Acids as Nucleophiles. FEBS Letters, 1993. 329(1-2), pp. 40-42.
Shiro Akabori, et al., Protection of Amide-Nitrogen for Peptide Systhesis. A Novel Synthesis of Peptides Containing C-Terminal Glutamine, Bull. Chem. Soc. Jpn., vol. 34, p. 739, May 1961.
Yasutsugu Shimonishi, et al., Studies on the Synthesis of Peptides Containing Glutamine as the C-Terminal. I. Protection of Amide-nitrogen with Xanthyl Group during Peptide Synthesis, Bull. Chem. Soc. Jpn., vol. 35, No. 12, pp. 1966-1970, 1962.
Yasutsugu Shimonishi, Studies of the Synthesis of Peptides Containing C-Terminal Glutamine. II. The Synthesis and Use of α-p-Nitrobenzyl γ-Methyl L-Glutamate, Bull. Chem. Soc. Jpn., vol. 37, No. 2 pp. 200-203, 1964.
Kazuyuki, Morihara, et al., α-Chymotrypsin as the Catalyst for Peptide Synthesis, Biochemical J., vol. 163, pp. 531-542, 1977.
U.S. Appl. No. 11/765,926, filed Jun. 20, 2007, Abe et al.

* cited by examiner

*Primary Examiner* — Ruth Davis
*Assistant Examiner* — Sheridan Macauley
(74) *Attorney, Agent, or Firm* — Oblon, Spivak, McClelland, Maier & Neustadt, L.L.P.

(57) ABSTRACT

The present invention provides a method for producing a dipeptide from starting materials that are available at low costs through a route industrially advantageous and simple. Dipeptides are produced from amino acid esters and amino acids by using a culture of a microbe having an ability to produce a dipeptide from an amino acid ester and an amino acid, microbial cells separated from the culture, or treated microbial cell product.

19 Claims, No Drawings

METHOD FOR PRODUCING DIPEPTIDES

TECHNICAL FIELD

The present invention relates to a method for producing dipeptides. More particularly, the present invention relates to a simple and cheaper method for producing dipeptides from amino acid esters and amino acids.

BACKGROUND ART

Dipeptides find uses in various fields. For example, the dipeptides are used as raw materials for pharmaceuticals and functional foods. Specifically, L-alanyl-L-glutamine is used as a component of serum-free media. L-alanyl-L-glutamine is also used as a component of solutions for infusion, because it is more stable and more soluble in water than L-glutamine.

The dipeptides are generally produced by chemical synthetic methods. However, such methods often require complicated steps. Examples of such method may include use of N-benzyloxycarbonylalanine (hereinafter referred to as "Z-alanine") and protected L-glutamine (Bull. Chem. Soc. Jpn., 34, 739 (1961) and Bull. Chem. Soc. Jpn., 35, 1966 (1962)); use of Z-alanine and protected L-glutamic acid-γ-methyl ester (Bull. Chem. Soc. Jpn., 37, 200 (1964)); use of Z-alanine ester and non-protected glutamine (JP-1-96194A); and synthesis using a 2-substituted propionyl halide as a raw material via N-(2-substituted)-propionylglutamine derivative as an intermediate (JP-6-234715A).

However, all of these methods require introduction and elimination of protective groups or synthesis of intermediates, so that none of them are industrially advantageous and fully satisfactory.

As typical production methods for producing dipeptides with enzymes, there have been known a condensation reaction using an N-protected-C-nonprotected carboxyl component and an N-nonprotected-C-protected amine component (hereinafter, "reaction 1") and a substitution reaction using an N-protected-C-protected carboxyl component and an N-nonprotected-C-protected amine component (hereinafter, "reaction 2"). An example of the reaction 1 is a method for producing a Z-aspartylphenylalanine methyl ester from Z-aspartic acid and phenylalanine methyl ester (JP-53-92729A). An example of the reaction 2 is a method for producing acetylphenylalanylleucinamide from acetylphenylalanine ethyl ester and leucinamide (Biochemical J., 163, 531 (1977)). There are very few reports as to use of an N-nonprotected-C-protected carboxyl component. An example of a substitution reaction using an N-nonprotected-C-protected carboxyl component and an N-nonprotected-C-protected amine component (hereinafter, "reaction 3") includes, for example, a method for producing arginylleucinamide from arginine ethyl ester and leucinamide as described in WO90/01555. An example of a substitution reaction using an N-nonprotected-C-protected carboxyl component and an N-nonprotected-C-nonprotected amine component (hereinafter, "reaction 4") includes, for example, a method for producing tyrosylalanine from tyrosine ethyl ester and alanine as described in EP-278787A. Production methods that can be the most inexpensive among these production methods are those using reactions that fall within the category of the reaction 4 in which the number of the protective groups in the components used is the smallest.

However, enzymes used in the conventional example of the reaction 4 (EP-278787A) include reagents of relatively expensive carboxypeptidase preparations derived from yeast that belongs to the genus Saccharomyces or fungi or plants. The produced dipeptides contain amino acids with relatively high degrees of hydrophobicity. EP-278787A discloses no method that uses an enzyme derived from bacteria or yeast other than that belongs to the genus Saccharomyces. Further, no method has been known that produces alanylglutamine or alanylasparagine that has a high hydrophilicity. Thus, development of a production method for such peptides on an industrial scale and at a reduced cost has been demanded.

DISCLOSURE OF THE INVENTION

It is an object of the present invention to provide a method for producing a dipeptide using a starting material that is available at a reduced cost and an enzyme source that is supplied at a reduced cost (cultures of microbes, microbial cells, or treated microbial cell products) through a route that is industrially advantageous and simple.

As a result of extensive studies, the inventors of the present invention have found that microbes that belong to certain bacteria and yeasts and can be cultured at low costs have abilities to produce dipeptides from L-amino acid esters and L-amino acids that are available at a low cost, thus accomplishing the present invention.

That is, the present invention provides:

[1] A method for producing a dipeptide comprising:
reacting an amino acid ester with an amino acid to form the dipeptide in the presence of at least one selected from the group consisting of a culture of a microbe, microbial cells separated from the culture, a treated microbial cell product, and a peptide-forming enzyme derived from the microbe,
wherein the microbe has an ability to form the dipeptide from the amino acid ester and the amino acid and belongs to a genus selected from the group consisting of *Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodothermus, Zobellia, Muricauda, Salegentibacter, Taxeobacter, Cytophaga, Marinilabilia, Lewinella, Saprospira*, and *Haliscomenobacter*.

[2] The method according to [1] above, further comprising adding a metal enzyme inhibitor to a reaction mixture upon forming the dipeptide from the amino acid ester and the amino acid in the presence of at least one selected from the group consisting of the culture of the microbe, the microbial cells separated from the culture, the treated microbial cell product, and the peptide-forming enzyme derived from the microbe.

[3] The method according to [1] or [2] above, wherein the amino acid ester is an L-alanine ester.

[4] The method according to any one of [1] to [3] above, wherein the amino acid is L-glutamine.

The present invention provides a simple method for producing dipeptide at a low cost. According to the present invention, a dipeptide can be produced from an amino acid ester and an amino acid that are available at a low cost without undergoing complex synthesis processes, so that the cost for producing dipeptides that are useful as materials for pharmaceuticals and functional foods can be reduced. Moreover, various types of dipeptides can be produced from various kinds of amino acid esters and amino acids as raw materials.

BEST MODE FOR CARRYING OUT THE INVENTION

The method for producing a dipeptide according to the present invention uses one selected from the group consisting of a culture of a microbe, microbial cells separated from the culture, a treated microbial cell product, and a peptide-forming enzyme derived from the microbe, wherein the microbe has an ability to produce the dipeptide from an amino acid ester and an amino acid. Reaction involved in the method for producing a dipeptide according to the present invention is represented by the following reaction scheme. As illustrated in the following reaction scheme, "dipeptideo" used herein refers to a peptide polymer that has one peptide bond.

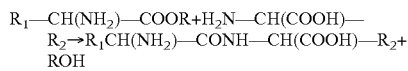

$$R_1\text{—CH(NH}_2\text{)—COOR} + H_2N\text{—CH(COOH)—}R_2 \rightarrow R_1CH(NH_2)\text{—CONH—CH(COOH)—}R_2 + ROH$$

(where R represents a substituted or unsubstituted hydrocarbon chain; $R_1$ represents a side chain of an amino acid ester; and $R_2$ represents a side chain of an amino acid.).

The amino acid ester is available at a low cost. The method of the present invention is a novel method for producing a dipeptide since the method utilizes an amino acid ester and a nonprotected amino acid as the starting materials that are reacted in an aqueous solution with a bacterium or a yeast as an enzyme source. This method thus makes it possible to provide a dipeptide that is useful as a material for pharmaceuticals and functional foods at a low cost.

The present method for producing the dipeptide will be explained in detail in the following order:

[I] Microbes having an ability to produce a dipeptide from an amino acid ester and an amino acid,

[II] Method for producing dipeptides, and

[III] Isolation and so forth of a DNA encoding a protein having a peptide-forming activity.

[I] Microbes having an Ability to Produce a Dipeptide from an Amino Acid Ester and an Amino Acid The microbes that may be used in the present invention are not particularly limited and any microbes that have an ability to produce a dipeptide from an amino acid ester and an amino acid may be used. The microbes that have an ability to produce a dipeptide from an amino acid ester and an amino acid may include those microbes that belong to the genus *Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodothermus, Zobellia, Muricauda, Salegentibacter, Taxeobacter, Cytophaga, Marinilabilia, Lewinella, Saprospira,* or *Haliscomenobacter*. Specifically, the following microbes are exemplified.

*Cellulophaga lytica* NBRC 14961
*Weeksella virosa* NBRC 16016
*Pedobacter heparinus* NBRC 12017
*Persicobacter diffluens* NBRC 15940
*Flexithrix dorotheae* NBRC 15987
*Chitinophaga pinensis* NBRC 15968
*Cyclobacterium marinum* ATCC 25205
*Runella slithyformis* ATCC 29530
*Thermonema lapsum* ATCC 43542
*Psychroserpens burtonensis* ATCC 700359
*Gelidibacter algens* ATCC 700364
*Dyadobacter fermentans* ATCC 700827
*Flammeovirga aprica* NBRC 15941
*Spirosoma linguale* DSMZ 74
*Flectobacillus major* DSMZ 103
*Tenacibaculum maritimum* ATCC 43398
*Rhodothermus marinus* DSMZ 4252
*Zobellia galactanivorans* DSMZ 12802
*Muricauda ruestringensis* DSMZ 13258
*Salegentibacter salegens* DSMZ 5424
*Taxeobacter gelupurpurascens* DSMZ 11116
*Cytophaga hutchinsonii* NBRC 15051
*Marinilabilia salmonicolor* NBRC 15948
*Lewinella cohaerens* ATCC 23123
*Saprospira grandis* ATCC 23119
*Haliscomenobacter hydrossis* ATCC 27775

Among the aforementioned strains, those with ATCC numbers have been deposited at American Type Culture Collection (P.O. Box 1549, Manassas Va. 20110, U.S.A.) and may be furnished by referring to the respective numbers. Among the aforementioned strains, those with NBRC numbers have been deposited at the NITE Biological Resource Center, Department of Biotechnology, National Institute of Technology and Evaluation (5-8 Kazusa-Kamaashi 2-Chome, Kisarazu-shi, Chiba-ken, 292-0818 Japan), and may be furnished by referring to each number. Among the aforementioned strains, those with DSMZ numbers have been deposited at the Deutche Sammlung von Mikroorganismen und Zelikulturen GmbH (German Collection of Microbes and Cell Cultures) (Mascheroder Weg 1b, 38124 Braunschweig, Germany), and may be furnished by referring to each number.

Either wild strains or mutant strains may be used as the microbes. Recombinant strains that are induced by genetic techniques such as cell fusion or genetic engineering and so forth may also be used as the microbes.

Cells of such a microbe may be obtained by cultivating the microbe in a proper medium to cause proliferation. The medium may be any medium that allows the microbe to proliferate. For example, the medium may be an ordinary medium that contains a carbon source, a nitrogen source, a phosphorus source, a sulfur source, and inorganic ions. If necessary, the medium may further contain an organic nutrient source that is commonly used.

For example, as the carbon source, any carbon source may be used so far as the above-mentioned microbe can utilize it. Specifically, sugars such as glucose, fructose, maltose, and amylose; alcohols such as sorbitol, ethanol, and glycerol; organic acids such as fumaric acid, citric acid, acetic acid, and propionic acid as well as salts thereof; hydrocarbons such as paraffin; or mixtures thereof may be used.

As the nitrogen source, ammonium salts of inorganic acids, such as ammonium sulfate and ammonium chloride; ammonium salts of organic acids, such as ammonium fumarate and ammonium citrate; nitrates such as sodium nitrate and potassium nitrate; organic nitrogen compounds such as peptone, yeast extracts, meat extracts and corn steep liquor; or mixtures of these may be used.

If necessary, the medium may also contain nutrient sources that are used in ordinary media such as inorganic salts, trace metal salts, and vitamins.

Cultivation conditions are not particularly limited. For example, cultivation may be performed under aerobic conditions with properly controlling pH and temperature within the ranges of a pH 5 to 8 and 5° C. to 65° C. for from about 12 hours to about 100 hours.

[II] Method for Producing Dipeptides

The method for producing a dipeptide according to the present invention includes a step of reacting an amino acid ester with an amino acid to form the dipeptide in the presence of at least one selected from the group consisting of a culture of a microbe that has an ability to produce a dipeptide from an amino acid ester and an amino acid, microbial cells separated from the culture, a treated microbial cell product, and a peptide-forming enzyme derived from the microbe. The peptide-forming enzyme produced by the microbe has an activity to produce a dipeptide from an amino acid ester and an amino acid as substrates.

The peptide-forming enzyme produced by the microbe may be brought into reaction with the amino acid ester and amino acid by directly adding the substrates to a liquid in which the above-mentioned microbe is being cultivated. Alternatively, the cells may be separated by centrifugation from the cultured liquid or the cultured microbes after completing the cultivation. The separated cells as they are, or the separated cells after being washed may be resuspended in a buffer, and the amino acid ester and amino acid may be added thereto for performing the reaction. Alternatively, cells immobilized by a conventional method such as a polyacrylamide gel method, a carrageenan method or an alginate gel method may be used.

It is possible to employ disrupted cells fragments, acetone-treated microbial cells, or freeze-dried microbial cells as the treated microbial cell product. The disruption may be performed by ultrasonic disruption, French press disruption, glass bead disruption or the like. Further, in the case where lysis is desired, a method using egg white lysozyme, a method using peptidase treatment or suitable combinations thereof may be used. Further, a peptide-forming enzyme may be recovered from the treated microbial cell product, to obtain a crude enzyme solution for use. If necessary, the crude enzyme may be purified before use. As the method for purifying the enzyme from the culture, an ordinary enzyme purification method may be used. Specifically, the above-mentioned peptide-forming enzyme may be purified through the following steps; recovering cells by centrifugation or the like, disrupting the cells by a mechanical method such as ultrasonic treatment, glass bead treatment, or dyno mill treatment, removing solid matter such as cell debris by centrifugation to obtain a crude enzyme, and then performing ultracentrifugal fractionation, salting out, organic solvent precipitation, ion exchange chromatography, adsorption chromatography, gel filtration, or hydrophobicity chromatography or the like.

Note that "peptide-forming enzyme derived from a microbe" includes not only an enzyme obtained by the above-mentioned purification step from the treated microbial cell product but also enzymes produced by expressing gene of the enzyme in a heterogeneous or homogeneous strain host, i.e., produced by a so-called a genetic engineering technique.

That is, an enzyme and all those enzyme-containing products may be used so far as they are fractions that have an activity to produce a dipeptide from an amino acid ester and an amino acid. The "enzyme-containing products" as used herein may be any products that contain the enzyme. Specific embodiments thereof may include a culture of the microbe that produces the enzyme, the microbial cells separated from the culture, the treated microbial cell product and so forth. The culture of the microbe refers to any matters that are obtainable by cultivating a microbe. Specifically, the culture of the microbe may be a mixture of microbial cells, a medium used for cultivating the microbe, and a substance produced by the cultivated microbe. Further, the microbial cells may be washed to obtain washed microbial cells for use. Furthermore, the treated cell product may include disrupted microbial cells, lysed microbial cells, freeze-dried microbial cells and so forth. The treated cell product may still further include a crude enzyme recovered by treating the microbial cells and a purified enzyme obtained by further purifying the crude enzyme. As the purified enzyme, partially purified enzymes obtained by various purification methods may be used. The enzymes may further be immobilized by a further procedure such as a covalent bond method, an adsorption method, and an inclusion method, to obtain an immobilized enzyme that may also be used. When some microbes are partly lysed during cultivation, culture supernatant may also be utilized as the enzyme-containing product.

The culture, cultivated microbial cells, washed microbial cells, and treated microbial cells obtained by disrupting and lyzing microbial cells often contain enzymes that do not participate in production of peptides but decompose the produced peptide. Therefore, upon using them, it is sometimes preferable to add a metal enzyme inhibitor such as a metal protease inhibitor such as ethylenediaminetetraacetic acid (EDTA). Addition amount thereof may be in the range of from 0.1 mM to 100 mM, preferably from 1 mM to 50 mM.

The amount of the enzyme or enzyme containing-products to be used may be in a range of an effective amount, i.e., an amount with which a desired effect is obtainable. The effective amount may be readily determined by a person having ordinary skill in the art by conducting a simple preliminary experiment. For example, in the case where the washed microbial cells are used, the preferable amount of the washed microbial cells to be used may be 0.1 g to 500 g per liter of the reaction mixture.

The amino acid ester to be used may be any amino acid ester as far as the peptide-forming enzyme specifically utilizes the amino acid ester together with an amino acid for producing a dipeptide. Examples thereof may include methyl esters, ethyl esters, n-propyl esters, isopropyl esters, n-butyl esters, isobutyl esters, tert-butyl esters, etc. of L-amino acids. Not only L-amino acid esters that correspond to natural type amino acids but also L-amino acid esters or D-amino acid esters that correspond to nonnatural type amino acids or derivatives thereof may also be used. In the present invention, L-alanine esters may preferably be used as the amino acid esters.

The amino acid is not particularly limited and any known amino acid may be used so far as the peptide-forming enzyme specifically utilizes the amino acid together with the amino acid ester for producing the dipeptide. Both L-amino acids and D-amino acids may be used. More specific examples thereof may be C-nonprotected L-amino acids, C-protected L-amino acids, C-nonprotected D-amino acids, C-protected D-amino acids, amines and so forth. Further, as the amines, not only natural type amines but also nonnatural type amines or derivatives thereof may be exemplified. Furthermore, as the amino acids, not only natural type amino acids but also nonnatural type amino acids or derivatives thereof may be exemplified. In addition to α-amino acids, β-, γ-, ω-, etc. amino acids may also be exemplified. In the present invention, preferably L-glutamine may be used as the amino acid.

Concentrations of the starting materials, i.e. the amino acid ester and amino acid, are each from 1 mM to 10 M, preferably from 0.05 M to 2 M. In some cases, it is preferable that the amino acid is added in an amount equimolar or excess molar with respect to the amino acid ester. If necessary, the substrate may be added step-wisely to the reaction system. For example, if a particular substrate may inhibit the reaction at a high concentration, such a substrate may be added step-wisely for keeping the concentration thereof below such an inhibitory level.

Reaction temperature may be from 3° C. to 70° C., and preferably from 5° C. to 50° C. Reaction pH is from 2 to 12, and preferably 3 to 11. By performing the reaction for 2 to 100 hours, a dipeptide may be produced and accumulated in the reaction mixture. The produced dipeptide may be recovered by a conventional method and, if necessary, purified.

[III] Isolation and so forth of DNA Encoding a Protein that has Peptide-forming Activity

[III-1] Isolation of DNA

The microbes used in the present invention have an ability to form dipeptides from amino acid esters and amino acids. It is possible to isolate from such microbes a DNA encoding a protein having an ability to produce the dipeptide from the amino acid esters and the amino acid with a genetic engineering technique. The isolated DNA may further be used to construct transformants that produce the protein having the ability to produce the dipeptide from the amino acid ester and the amino acid (peptide-forming enzyme). The following is an embodiment of a method for isolating a DNA encoding a protein that produces a dipeptide from an L-amino acid ester and an L-amino acid from a microbe and making a transformant.

First, a peptide-forming enzyme is obtained from the above-mentioned microbe as described in [II] above. Then, amino acid sequence of the purified peptide-forming enzyme is determined. Such a determination may be performed by the Edman method (Edman, P., Acta Chem., Scand., 4, 227 (1950)) or by using a sequencer manufactured by Applied Biosynstems, Inc. As to the purified peptide-forming enzyme, the sequence of 30 amino acid residues from the N-terminal is determined. Based on the determined amino acid sequence, the base sequence of the DNA that encodes the peptide-forming enzyme may be deduced. The universal codons are adopted for deducing the base sequence of the DNA.

Based on the deduced base sequence, a DNA molecule of about 30 base pairs is synthesized. Method for synthesizing the DNA molecule is disclosed in Tetrahedron Letters, 22, 1859 (1981)). Alternatively, the DNA molecule may be synthesized by using a synthesizer manufactured by Applied Biosystems, Inc. The DNA molecule may be utilized as a probe for isolating a full-length DNA encoding the peptide-forming enzyme from the chromosome gene library of a microbe. Alternatively, the DNA molecule may be used as a primer when a DNA encoding a peptide-forming enzyme is amplified by a PCR method. However, the DNA that is amplified by using the PCR method does not contain a full-length DNA encoding the peptide-forming enzyme, so that the full-length DNA encoding the peptide-forming enzyme is isolated from the chromosome gene library of the microbe by using the DNA that has been amplified by the PCR method as a probe.

The operations for the PCR method is described in White, T. J. et al., Trends Genet., 5, 185 (1989), etc. The method for preparing a chromosomal DNA and the method for isolating a target DNA molecule from a gene library are described in "Molecular Cloning", 2nd edition, Cold Spring Harbor Press (1989), etc.

The method for determining the base sequence of a DNA encoding the isolated peptide-forming enzyme is described in "A Practical Guide to Molecular Cloning", John Wiley & Sons, Inc. (1985). Further, the base sequence may be determined by using a sequencer manufactured by Applied Biosystems, Inc.

The DNA that may be used in the present invention is not limited to the DNAs obtained as described above. The DNA to be used may also include any DNAs as long as it encodes the peptide-forming enzyme, even if the DNA is an artificially mutated DNA obtained by mutating a DNA encoding the peptide-forming enzyme that has been isolated from a chromosomal DNA of a certain microbe. The method that is frequently used as a method for such an artificial mutation may be a site-specific mutagenesis as described in Method. in Enzymol., 154 (1987).

The DNA that may be used in the present invention may also include a DNA having a base sequence that hybridizes with a polynucleotide (DNA or RNA) having a base sequence complementary to the base sequence of the DNA that has been isolated from a DNA such as a chromosomal DNA as described above under a stringent condition and encoding the protein having the peptide-forming activity.

The term "under a stringent condition" as used herein refers to a condition under which a so-called specific hybrid is formed but no non-specific hybrid is formed. Although it is difficult to precisely express this condition in numerical values, the examples of such conditions may be a condition under which DNAs having a high homology, for example, 50% or more, preferably 80% or more, more preferably 90% or more, hybridize with each other and DNAs having a lower homology than these do not hybridize with each other, or ordinary conditions for rinsing in Southern hybridization, that is, hybridization at 60° C. in a salt concentration corresponding to 1×SSC and 0.1% SDS, preferably 60° C., 0.1× SSC, and 0.1% SDS, more preferably 65° C., 0.1×SSC, and 0.1% SDS. The activity of the peptide-forming enzyme is as already explained above. However, as to the base sequence that hybridizes with a complementary base sequence under a stringent condition, it is desirable that the protein encoded thereby retain an enzyme activity of about 50% or more, more preferably 80% or more, further preferably 90% or more of the enzyme activity of the protein having the original amino acid sequence under conditions of 50° C. and pH 8.

Further, proteins that are substantially the same as the protein encoded by the isolated DNA may also be used in the present invention. Therefore, the DNA to be used in the present invention may also include a DNA encoding a protein that contains substitution, deletion, insertion, addition and/or inversion of one or a plurality of amino acid residues in the amino acid sequence encoded by the isolated DNA and that has a peptide-forming activity, i.e., that has an ability to catalyze a reaction for producing the dipeptide from an L-amino acid ester and an L-amino acid. The term "plurality" herein means the range of the number of amino acid residues that causes no significant damage on the three-dimensional structure of protein or activity of peptide-forming enzyme. Specifically, "plurality" usually means from 2 to 50, preferably 2 to 30, more preferably 2 to 10. The activity of the peptide-forming enzyme is as already explained above. However, as to the amino acid sequence that contains substitution, deletion, insertion, addition and/or inversion of one or a plurality of amino acid residues, it is desirable that such an amino acid sequence retains an enzyme activity of 50% or more, more preferably 80% or more, and further preferably 90% or more of that of the protein having the original amino acid sequence under conditions of 50° C. and pH 8.

As described above, when a DNA is isolated from a microbe, the following DNAs may preferably be used in the present invention. In the following examples, the specified base sequence of the isolated DNA is referred to as the base sequence y, and the amino acid sequence encoded by the base sequence is referred to as the amino acid sequence Y. The DNAs that may be used in the present invention include:
  (i) A DNA consisting of the base sequence y,
  (ii) A DNA that hybridizes with a polynucleotide consisting of a base sequence complementary to the base sequence y under the stringent condition and that encodes a protein having a peptide-forming activity that catalyzes a reaction to produce a dipeptide from an L-amino acid ester and an L-amino acid,
  (iii) A DNA that encodes a protein having the amino acid sequence Y, and
  (iv) A DNA that encodes a protein having an amino acid sequence corresponding to the amino acid sequence Y that contains substitution, deletion, insertion, addition and/or inversion of one or a plurality of amino acid residues and having a peptide-forming activity that catalyzes a reaction to produce a dipeptide from an L-amino acid ester and an L-amino acid.

[III-2] Preparation of Transformants

Subsequently, the construction of the transformants that express the protein having the peptide-forming activity will be explained. There are a number of known examples of production for obtaining useful proteins such as enzymes and physiologically active substances utilizing a recombinant DNA technology. Use of the recombinant DNA technology enables mass production of useful proteins existing in minute amounts in nature.

Preferable examples of the transformants that may be used in the method of the present invention include transformants that can express proteins such as those described in (A), (B) or (C) below:

(A) A protein that has the amino acid sequence Y,
(B) A protein that has an amino acid sequence corresponding to the amino acid sequence Y that contains substitution, deletion, insertion, addition and/or inversion of one or a plurality of amino acid residues and has a peptide-forming activity that catalyzes a reaction to produce a dipeptide from an L-amino acid ester and an L-amino acid, and
(C) A protein encoded by a DNA that hybridizes with a polynucleotide consisting of a base sequence complementary to the base sequence y under the stringent condition and encodes a protein having a peptide-forming activity that catalyzes a reaction to produce a dipeptide from an L-amino acid ester and an L-amino acid.

The transformants that express proteins (A) to (C) having a peptide-forming activity may be produced by introducing any of DNAs (i), (ii), (iii) and (iv) discussed in [III-1] above. That is, the DNA of (i), (ii), (iii) or (iv) may be incorporated into an expression vector that can be expressed in the host cell and introduced in the host cell.

The mutation as mentioned in (B) above may be obtained by, for example, a site-directed mutagenesis by which the base sequence of the gene of the present enzyme is modified so that the encoded amino acid at a particular site of the gene of the enzyme is substituted, deleted, inserted or added. The modified DNA as described above may also be obtained by a conventionally known mutation treatment. Examples of such a mutation treatment may include, for example, an in vitro treatment of the DNA encoding the present enzyme with hydroxylamine or the like, and a treatment of a bacterium of the genus *Escherichia* possessing a DNA encoding the present enzyme with a mutagen that is conventionally used for artificial mutation, such as ultraviolet ray, N-methyl-N'-nitro-N-nitrosoguanidine (NTG), or nitrous acid.

In one of the preferable embodiments of mass-production of the protein with the recombinant DNA technology, the protein molecules may associate to form an inclusion body of the protein in the transformant producing the protein. The advantage of this expression and production manner may be the protection of the objective protein from digestion due to proteases that exist in the microbial cells, and ready purification of the objective protein by disruption of the microbial cells and subsequent centrifugation operation.

The inclusion body of the protein thus obtained may be solubilized with a protein modifier. The solubilized protein may then be subjected to an activating reconstitution by, e.g. removing the modifier, to be converted into a properly-folded, physiologically active protein. There are many examples thereof, such as re-activation of human interleukin-2 (JP-61-257931A).

Retrieval of the activated type protein from the inclusion body of the protein may require a series of operations such as solubilization and activating reconstitution, which may make the operation more complicated than that in direct production of the active type protein. However, if the protein to be produced in the microbial cells may affect growth of the cells, accumulation of the protein in the form of such an inactive inclusion body in the cells may contribute to suppress influence of such a protein on the cells.

Production of the objective protein as the inclusion body on a large scale may be performed by simple expression of the objective protein under the control of a potent promoter, as well as expression of a fused protein consisting of the objective protein and another protein that is known to be expressed in a large amount.

Further, it may be useful to incorporate a sequence that is recognizable by a restriction protease into a suitable position for cutting out the objective protein after the expression of the fused protein.

When a protein is mass-produced by using the recombinant DNA technology, the host cells to be transformed may be bacteria cells, actinomycetes cells, yeast cells, fungi cells, plant cells, animal cells and the like. Among them, enterobacteria, preferably *Escherichia coli*, may be used as the host cells, because there is a lot of findings about the technology of mass production of proteins by using enterobacteria such as *Escherichia coli*. One embodiment of the production of the peptide-forming enzyme with transformed *Escherichia coli* bacteria will be described hereinbelow.

Promoter to be used for expressing the DNA that encodes a peptide-forming enzyme may include promoters that are usually used in the production of heterogeneous protein in *Escherichia coli*. Examples of such a promoter may include potent promoters such as a T7 promoter, a lac promoter, a trp promoter, a trc promoter, a tac promoter, and $P_R$ and $P_L$ promoters of a lambda phage.

In order to produce the peptide-forming enzyme as an inclusion body of fused protein, a gene that encodes another protein, preferably a hydrophilic peptide may be ligated to upstream or downstream of the peptide-forming enzyme gene to form a fused protein gene. The gene that encodes such other protein may be any gene that increases an accumulation amount of the fused protein and enhances the solubility of the fused protein after modification and reconstitution step. Candidates therefor may include, for example, a T7 gene 10, a β-galactosidase gene, a dehydrofolic acid reductase gene, an interferon-γ gene, an interleukin-2 gene, and a prochymosin gene.

For ligation of these genes to the genes encoding the peptide-forming enzymes, reading frames of codons thereof should correspond to each other. Such a correspondence may be achieved by the ligation at a suitable restriction enzyme site, or by utilizing a synthetic DNA having a suitable sequence be utilized.

In order to increase the production amount of the peptide-forming enzyme, it is preferable in some cases to ligate terminator, which is a transcription terminating sequence, to the downstream of the fusion protein gene. The terminator may include, for example, a T7 terminator, an fd phage terminator, a T4 terminator, a tetracycline resistant gene terminator, and an *Escherichia coli* trpA gene terminator.

As the vectors for introducing the gene that encodes a peptide-forming enzyme or a fused protein consisting of the peptide-forming enzyme and another protein into *Escherichia coli,* so-called multi-copy type vectors are preferable. Examples thereof may include a plasmid having a replication origin derived from ColE1, for example, a pUC-based plasmid, and a pBR322-based plasmid or derivatives thereof. The "derivatives" as used herein refer to those plasmids that have been subjected to modification by substitution, deletion, insertion, addition or inversion of bases. The modification as used herein may include modifications by a mutation treatment with a mutagen or UV irradiation, or modifications by spontaneous mutation. More specifically, the vectors to be used may include pUC 19, pUC18, pBR322, pHSG299, pHSG298, pHSG399, pHSG398, RSF1010, pMW119, pMW118, pMW219, pMW218 and so forth. Besides, vectors such as phage DNAs and transposon DNA may also be used.

For facilitating screening of the transformants, it is preferable that the vectors have markers such as an ampicillin resistant gene. Such plasmids are commercially available as expression vectors having potent promoters (a pUC-based vector (manufactured by Takara Shuzo, Co., Ltd.), pRROK-based vector (manufactured by Clonetech Laboratories, Inc.), pKK233-2 (manufactured by Clonetech Laboratories, Inc.) and so forth).

A recombinant DNA may be obtained by ligating the promoter, the gene encoding the peptide-forming enzyme or the fused protein of the peptide-forming enzyme and another protein, and the terminator in this order to give a DNA fragment, and further ligating the same to a vector DNA. Transformation of Escherichia coli with the recombinant DNA, and cultivation of the bacteria result in expression and production of the peptide-forming enzyme or the fused protein of the peptide-forming enzyme and another protein. The host to be transformed may be of any strains that are usually used in expressing a heterogeneous gene. For example, Escherichia coli JM109 strain is preferable. The method for performing transformation and the method for screening the transformants are described in, for example, Molecular Cloning, 2nd edition, Cold Spring Harbor Press (1989).

When the peptide-forming enzyme is expressed as a fused protein, the fused protein may be designed so that the peptide-forming enzyme can be cut out of the fused protein by a restriction protease that recognizes a sequence not existent in the peptide-forming enzyme as a recognition sequence, such as a blood coagulation factor Xa or kallikrein.

The production media to be used may be any of those media that are usually used for cultivating Escherichia coli, such as M9-casamino acid medium and LB medium. Further, the conditions for cultivation and induction of the production may suitably be selected depending on the kinds of the marker and promoter of the employed vector, and of the host microbe.

The peptide-forming enzyme or the fused protein of the peptide-forming enzyme and another protein may be recovered by, for example, the following methods: If the peptide-forming enzyme or the fused protein thereof is solubilized in the microbial cells, a crude enzyme solution for use may be obtained by recovery of the microbial cells and subsequent disruption or lysis thereof. If necessary, the crude solution may be purified by, e.g., an ordinary precipitation, filtration and column chromatography for obtaining the purified peptide-forming enzyme or fused protein thereof for use. In this case, a purification method that utilizes an antibody to the peptide-forming enzyme or fused protein thereof may also be used.

When the inclusion bodies of the protein are formed, the inclusion bodies of protein may be solubilized with the modifier. The peptide-forming enzyme may be solubilized together with the microbial cell proteins. However, taking the subsequent purification operations into consideration, it is preferable to take the inclusion bodies out of the microbial cells and then solubilize the inclusion bodies. Recovery of the inclusion bodies from the microbial cells may be performed by a conventionally known method. For example, the microbial cells may be disrupted and the inclusion bodies may be recovered by centrifugation or the like. The modifier for solubilizing the inclusion bodies of the protein may include, for example, guanidine hydrochloride (for example, 6 M, pH 5 to 8) or urea (for example, 8 M).

By removing the modifier by the operations such as dialysis, the protein may be reconstituted as an active form. Examples of the solution for dialysis may include, for example, Tris-HCl buffer and phosphate buffer. The concentration and pH thereof may be 20 mM to 0.5 M and pH 5 to 8, respectively.

Concentration of the protein at the reconstitution step is preferably retained at about 500 μm/ml or less. In order to avoid self cross-linking of the reconstituted peptide-forming enzyme, it is preferable to keep the dialysis temperature at 5° C. or less. The method for removing the modifier other than the dialysis method may include a dilution method, an ultra-filtration method, and so forth. The activity will be regenerated by using any one of these methods.

The genetic engineering techniques may be practiced based on the techniques described in literature, such as, for example, Molecular Cloning, 2nd edition, Cold Spring Harbor Press (1989).

EXAMPLE

The present invention will be described in more detail with reference to the Examples hereinbelow. However, the present invention should not be considered to be limited to these Examples. In these Examples, L-alanine and L-alanyl-L-glutamine were quantified by high performance liquid chromatography (column: InertsiL ODS-2 manufactured by GL Science, Inc.; eluant: aqueous phosphoric acid solution (pH 2.2, 5.0 mM sodium 1-octanesulfonate/methanol=100/15, flow rate: 1.0 ml/min, detection: 210 nm)).

Example 1

Microbes that Produce L-alanyl-L-glutamine

Cultivation of *Cellulophaga lytica* NBRC 14961 and *Flexithrix dorotheae* NBRC 15987 was performed with a solid agar medium (pH 7.2, sterilized at 120° C. for 15 minutes) containing 1 g of tryptone, 1 g of yeast extract and 15 g of agar in 1 L of DAIGO artificial sea water SP (manufactured by Nihon Pharmaceutical Co., Ltd). Cells of *Cellulophaga lytica* NBRC 14961 or *Flexithrix dorotheae* NBRC 15987 were pre-cultured with the medium at 30° C. for 48 hours, and the cultured cells were then applied to the same medium for mass cultivation at 30° C. for 48 hours.

Cultivation of *Weeksella virosa* NBRC 16016 was performed with a sheep blood agar medium (Nissui Plate, manufactured by Nissui Pharmaceutical Co., Ltd). Cells of *Weeksella virosa* NBRC 16016 were pre-cultured with the medium at 30° C. for 48 hours, and the cultured cells were then applied to the same medium for mass cultivation at 30° C. for 48 hours.

Cultivation of *Pedobacter heparinus* NBRC 12017 was performed with a solid agar medium (pH 7.0, sterilized at 120° C. for 15 minutes) containing 10 g of peptone, 2 g of yeast extract, 1 g of $MgSO_4 \cdot 7H_2O$ and 15 g of agar in 1 L of distilled water. *Pedobacter heparinus* NBRC 12017 were pre-cultured with the medium at 30° C. for 48 hours, and the cultured cells were then applied to the same medium for mass cultivation at 30° C. for 48 hours.

Cultivation of *Persicobacter diffluens* NBRC 15940 was performed with a solid agar medium (pH 7.0, sterilized at 120° C. for 15 minutes) containing 0.5 g of $KNO_3$, 0.1 g of sodium glycerophosphate, 1 g of trishydroxymethylaminomethane, 5 g of tryptone, 5 g of yeast extract, 15 g of agar and 1 ml of a trace element solution in 1 L of DAIGO artificial sea water SP. The trace element solution contains 2.85 g of $H_3BO_4$, 1.8 g of $MnCl_2.4H_2O$, 1.36 g of $FeSO_4.7H_2O$, 26.9 mg of $CuCl_2.2H_2O$, 20.8 mg of $ZnCl_2$, 40.4 mg of $CoCl_2.6H_2O$, 25.2 mg of $Na_2MoO_4.2H_2O$, and 1.77 g of sodium tartarate in 1 L of distilled water. Cells of *Persicobacter diffluens* NBRC 15940 were pre-cultured with the medium at 25° C. for 48 hours, and the cultured cells were then applied to the same medium for mass cultivation at 25° C. for 48 hours.

Cultivation of *Chitinophaga pinensis* NBRC 15968 was performed with a solid agar medium (pH 7.0, sterilized at 120° C. for 15 minutes) containing 3 g of bacto-casitone, 1 g of yeast extract, 1.36 g of $CaCl_2.2H_2O$ and 15 g of agar in 1 L of distilled water. Cells of *Chitinophaga pinensis* NBRC 15968 were pre-cultured with the medium at 25° C. for 48 hours, and the cultured cells were then applied to the same medium for mass cultivation at 25° C. for 48 hours.

Cultivation of *Cyclobacterium marinum* ATCC 25205 was performed with a solid agar medium (pH 7.0, sterilized at 120° C. for 15 minutes) containing 5 g of peptone, 1 g of yeast extract, 0.2 g of $FeSO_4.7H_2O$ and 15 g of agar in 1 L of DAIGO artificial sea water SP. Cells of *Cyclobacterium marinum* ATCC 25205 were pre-cultured with the medium at 25° C. for 48 hours, and the cultured cells were then applied to the same medium for mass cultivation at 25° C. for 48 hours.

Cultivation of *Runella slithyformis* ATCC 29530 was performed with a solid agar medium (pH 7.0, sterilized at 120° C. for 15 minutes) containing 1 g of peptone, 1 g of yeast extract, 1 g of glucose and 15 g of agar in 1 L of distilled water. Cells of *Runella slithyformis* ATCC 29530 were pre-cultured with the medium at 25° C. for 48 hours, and the cultured cells were then applied to the same medium for mass cultivation at 25° C. for 48 hours.

Cultivation of *Thermonema lapsum* ATCC 43542 was performed with a solid agar medium (pH 8.2, sterilized at 120° C. for 15 minutes) containing 0.2 g of Nitrilotriacetic acid, 2 ml of 0.03% $FeCl_3$ solution, 0.12 g of $CaSO_4.2H_2O$, 0.2 g of $MgSO_4.7H_2O$, 0.016 g of NaCl, 0.21 g of $KNO_3$, 1.4 g of $NaNO_3$, 0.22 g of $Na_2HPO_4$, 2 ml of a trace element solution, and 15 g of agar in 1 L of distilled water. The trace element solution contains 0.5 ml of $H_2SO_4$, 2.2 g of $MnSO_4$, 0.5 g of $ZnSO_4$, 0.5 g of $H_3BO_3$, 0.016 g of $CuSO_4$, 0.025 g of $Na_2MoO_4$, and 0.046 g of $CoCl_2$ in 1 L of distilled water. Cells of *Thermonema lapsum* ATCC 43542 were pre-cultured with the medium at 60° C. for 48 hours, and the cultured cells were then applied to the same medium for mass cultivation at 60° C. for 48 hours.

Cultivation of *Gelidibacter algens* ATCC 700364, *Lewinella cohaerens* ATCC 23123, *Psychroserpens burtonensis* ATCC 700359 and *Salegentibacter salegens* DSMZ 5424 was performed with Marine Agar 2216 (manufactured by Difco). Cells of *Gelidibacter algens* ATCC 700364 or *Psychroserpens burtonensis* ATCC 700359 were pre-cultured with the medium at 10° C. for 72 hours, and the cultured cells were then applied to the same medium for mass cultivation at 10° C. for 72 hours. Cells of *Lewinella cohaerens* ATCC 23123 were pre-cultured with the medium at 30° C. for 48 hours, and the cultured cells were then applied to the same medium for mass cultivation at 30° C. for 48 hours. Cells of *Salegentibacter salegens* DSMZ 5424 were pre-cultured with the medium at 25° C. for 48 hours, and the cultured cells were then applied to the same medium for mass cultivation at 25° C. for 48 hours.

Cultivation of *Dyadobacter fermentans* ATCC 700827 was performed with a solid agar medium (pH 7.0, sterilized at 120° C. for 15 minutes) containing 0.8 g of $NH_4Cl$, 0.25 g of $KH_2PO_4$, 0.4 g of $K_2HPO_4$, 0.505 g of $KNO_3$, 15 mg of $CaCl_2.2H_2O$, 20 mg of $MgCl_2.6H_2O$, 7 mg of $FeSO_4.7H_2O$, 5 mg of $Na_2SO_4$, 5 mg of $MnCl_2.4H_2O$, 0.5 mg of $H_3BO_3$, 0.5 mg of $ZnCl_2$, 0.5 mg of $COCl_2.6H_2O$, 0.5 mg of $NiSO_4.6H_2O$, 0.3 mg of $CuCl_2.2H_2O$, 10 mg of $Na_2MoO_4.2H_2O$, 0.5 g of yeast extract, 0.5 g of peptone, 0.5 g of casamino acids, 0.5 g of dextrose, 0.5 g of soluble starch, 0.5 g of sodium pyruvate, and 15 g of agar in 1 L of distilled water. Cells of *Dyadobacter fermentans* ATCC 700827 were pre-cultured with the medium at 25° C. for 48 hours, and the cultured cells were then applied to the same medium for mass cultivation at 25° C. for 48 hours.

Cultivation of *Flammeovirga aprica* NBRC 15941 was performed with a solid agar medium (pH 7.2, sterilized at 120° C. for 15 minutes) containing 2 g of tryptone, 0.5 g of beef extract, 0.5 g of yeast extract, 0.2 g of sodium acetate, and 15 g of agar in 1 L of DAIGO artificial sea water SP. Cells of *Flammeovirga aprica* NBRC 15941 were pre-cultured with the medium at 25° C. for 48 hours, and the cultured cells were then applied to the same medium for mass cultivation at 25° C. for 48 hours.

Cultivation of *Spirosoma linguale* DSMZ 74 and *Flectobacillus major* DSMZ 103 was performed with a solid agar medium (pH 7.0, sterilized at 120° C. for 15 minutes) containing 1 g of glucose, 1 g of peptone, 1 g of yeast extract, and 15 g of agar in 1 L of distilled water. Cells of *Spirosoma linguale* DSMZ 74 or *Flectobacillus major* DSMZ 103 were pre-cultured with the medium at 25° C. for 48 hours, and the cultured cells were then applied to the same medium for mass cultivation at 25° C. for 48 hours.

Cultivation of *Tenacibaculum maritimum* ATCC43398 was performed with a solid agar medium (pH 7.0, sterilized at 120° C. for 15 minutes) containing 0.5 g of tryptone, 0.5 g of yeast extract, 0.2 g of beef extract, 0.2 g of sodium acetate, and 15 g of agar in 700 ml of DAIGO artificial sea water SP. Cells of *Tenacibaculum maritimum* ATCC 43398 were pre-cultured with the medium at 25° C. for 48 hours, and the cultured cells were then applied to the same medium for mass cultivation at 25° C. for 48 hours.

Cultivation of *Rhodothermus marinus* DSMZ 4252 was performed with a solid agar medium (pH 7.2, sterilized at 120° C. for 15 minutes) containing 2.5 g of yeast extract, 2.5 g of tryptone, 100 mg of Nitrilotriacetic acid, 40 mg of $CaSO_4.2H_2O$, 200 mg of $MgCl_2.6H_2O$, 0.5 ml of 0.01 M Fe citrate, 0.5 ml of a trace element solution, 100 ml of phosphate buffer, 900 ml of distilled water, and 28 g of agar in 1 L of the medium. The trace element solution contains 12.8 g of Nitrilotriacetic acid, 1 g of $FeCl_2.4H_2O$, 0.5 g of $MnCl_2.4H_2O$, 0.3 g of $CoCl_2.4H_2O$, 50 mg of $CuCl_2.2H_2O$, 50 mg of $Na_2MoO_4.2H_2O$, 20 mg of $H_3BO_3$, and 20 mg of $NiCl_2.6H_2O$ in 1 L of distilled water. The phosphate buffer contains 5.44 g of $KH_2PO_4$, and 43 g $K_2HPO_4$ in 1 L of distilled water. Cells of *Rhodothermus marinus* DSMZ 4252 were pre-cultured with the medium at 60° C. for 48 hours, and the cultured cells were then applied to the same medium for mass cultivation at 60° C. for 48 hours.

Cultivation of *Zobellia galactanivorans* DSMZ 12802 was performed with a solid agar medium. (1.5% agar, pH 7.6, sterilized at 120° C. for 15 minutes) containing BACTO MARINE BROTH (DIFCO 2216). Cells of *Zobellia galactanivorans* DSMZ 12802 were pre-cultured with the medium at 30° C. for 48 hours, and the cultured cells were then applied to the same medium for mass cultivation at 30° C. for 48 hours.

Cultivation of *Muricauda ruestringensis* DSMZ 13258 was performed with a solid agar medium (pH 7.2, sterilized at 120° C. for 15 minutes) containing 1.5 g of yeast extract, 2.5 g of peptone, 2 g of hexadecane, 17.7 g of NaCl, 0.48 g of KCl, 3.4 g of $MgCl_2.6H_2O$, 4.46 g of $MgSO_4.7H_2O$, 0.98 g of $CaCl_2$, and 15 g of agar in 1 L of distilled water. Cells of *Muricauda ruestringensis* DSMZ 13258 were pre-cultured with the medium at 30° C. for 48 hours, and the cultured cells were then applied to the same medium for mass cultivation at 30° C. for 48 hours.

Cultivation of *Taxeobacter gelupurpurascens* DSMZ 11116 was performed with a solid agar medium (pH 7.2, sterilized at 120° C. for 15 minutes) containing 3 g of casitone, 1 g of yeast extract, 1.36 g of $CaCl_2.2H_2O$, and 15 g of agar in 1 L of distilled water. Cells of *Taxeobacter gelupurpurascens* DSMZ 11116 were pre-cultured with the medium at 30° C. for 48 hours, and the cultured cells were then applied to the same medium for mass cultivation at 30° C. for 48 hours.

Cultivation of *Cytophaga hutchinsonii* NBRC 15051 was performed with a solid agar medium (pH 7.2, sterilized at 120° C. for 15 minutes) containing 3 g of casitone, 1 g of yeast extract, 1.36 g of $CaCl_2.2H_2O$, 5 g of cellobiose, and 15 g of agar in 1 L of distilled water. Cells of *Cytophaga hutchinsonii* NBRC 15051 were pre-cultured with the medium at 30° C. for 48 hours, and the cultured cells were then applied to the same medium for mass cultivation at 30° C. for 48 hours.

Cultivation of *Marinilabilia salmonicolor* NBRC 15948 was performed with a solid agar medium (pH 7.2, sterilized at 120° C. for 15 minutes) containing 10 g of peptone, 2 g of yeast extract, 0.5 g of $MgSO_4.7H_2O$, and 15 g of agar in a mixture of 250 ml of distilled water and 750 ml of DAIGO artificial sea water SP. Cells of *Marinilabilia salmonicolor* NBRC 15948 were pre-cultured with the medium at 30° C. for 48 hours, and the cultured cells were then applied to the same medium for mass cultivation at 30° C. for 48 hours.

Cultivation of *Saprospira grandis* ATCC 23119 was performed with a solid agar medium (pH 7.0, sterilized at 120° C. for 15 minutes) containing 0.5 g of $KNO_3$, 0.1 g of sodium glycerophosphate, 1 g of trishydroxymethylaminomethane, 2 g of tryptone, 2 g of yeast extract, 15 g of agar, and 1 ml of a trace element solution in 1 L of DAIGO artificial sea water SP. The trace element solution contains 2.85 g of $H_3BO_4$, 1.8 g of $MnCl_2.4H_2O$, 1.36 g of $FeSO_4.7H_2O$, 26.9 mg of $CuCl_2.2H_2O$, 20.8 mg of $ZnCl_2$, 40.4 mg of $CoCl_2.6H_2O$, 25.2 mg of $Na_2MoO_42H_2O$, and 1.77 g of sodium tartrate in 1 L of distilled water. Cells of *Saprospira grandis* ATCC 23119 were pre-cultured with the medium at 30° C. for 48 hours, and the cultured cells were then applied to the same medium for mass cultivation at 30° C. for 48 hours.

Cultivation of *Haliscomenobacter hydrossis* ATCC 27775 was performed with a solid agar medium (pH 7.5, sterilized at 120° C. for 15 minutes) containing 27 mg of $KH_2PO_4$, 40 mg of $K_2HPO_4$, 40 mg of $Na_2HPO_4.2H_2O$, 50 mg of $CaCl_2.2H_2O$, 75 mg of $MgSO_4.7H_2O$, 5 mg of $FeCl_3.6H_2O$, 3 mg of $MnSO_4.H_2O$, 1.31 g of glutamic acid, 2.5 mg of Trypticase Soy Broth without glucose, 0.4 mg of thiamin, 0.01 mg of vitamin B12, 2 g of glucose, and 1 ml of a trace element solution in 1 L of distilled water. The trace element solution contains 0.1 g of $ZnSO_4.7H_2O$, 0.03 g of $MnCl_2.4H_2O$, 0.3 g of $H_3BO_3$, 0.2 g of $CoCl_2.6H_2O$, 0.01 g of $CuCl_2.2H_2O$, 0.02 g of $NiCl_2.6H_2O$, and 0.03 g of $Na_2MoO_4.H_2O$ in 1 L of distilled water. Cells of *Haliscomenobacter hydrossis* ATCC 27775 were pre-cultured with the medium at 25° C. for 48 hours, and the cultured cells were then applied to the same medium for mass cultivation at 25° C. for 48 hours.

Each strain of the microbial cells thus obtained was recovered from the agar media, and suspended in a 0.1 M borate buffer (pH 9.0) containing 10 mM EDTA so as to prepare a suspension containing 100 g/l of wet microbial cells. 0.1 ml of each microbial cell suspension was admixed with 0.1 ml of 100 mM borate buffer (pH 9.0) containing 10 mM EDTA, 200 mM L-alanine methyl ester hydrochloride and 400 mM L-glutamine to prepare a total volume 0.2 ml of the reaction mixture, which was then subjected to the reaction at 20° C. for the time period shown in Table 1. The amount (mM) of L-alanyl-L-glutamine (Ala-Gln) produced by each reaction is shown in Table 1.

TABLE 1

| Microbe | Reaction Time (hr) | Ala-Gln (mM) | Microbe | Reaction Time (hr) | Ala-Gln (mM) |
| --- | --- | --- | --- | --- | --- |
| *Cellulophaga lytica* NBRC 14961 | 1 | 0.10 | *Spirosoma linguale* DSMZ 74 | 1 | 2.26 |
| *Weeksella virosa* NBRC 16016 | 2 | 0.41 | *Flectobacillus major* DSMZ 103 | 1 | 3.86 |
| *Pedobacter heparinus* NBRC 12017 | 1 | 31.46 | *Tenacibaculum maritimum* ATCC43398 | 1 | 0.01 |
| *Persicobacter diffluens* NBRC 15940 | 1 | 1.51 | *Rhodothermus marinus* DSMZ 4252 | 1 | 0.11 |
| *Flexithrix dorotheae* NBRC 15987 | 1 | 12.04 | *Zobellia galactanivorans* DSMZ 12802 | 1 | 2.28 |
| *Chitinophaga pinensis* NBRC 15968 | 1 | 9.12 | *Muricauda ruestringensis* DSMZ 13258 | 1 | 9.61 |
| *Cyclobacterium marinum* ATCC 25205 | 1 | 3.69 | *Salegentibacter salegens* DSMZ 5424 | 1 | 0.40 |
| *Runella slithyformis* ATCC 29530 | 1 | 0.91 | *Taxeobacter gelupurpurascens* DSMZ 11116 | 2 | 0.10 |
| *Thermonema lapsum* ATCC 43542 | 2 | 0.04 | *Cytophaga hutchinsonii* NBRC 15051 | 2 | 0.01 |
| *Psychroserpens burtonensis* ATCC 700359 | 1 | 17.11 | *Marinilabilia salmonicolor* NBRC 15948 | 1 | 1.00 |
| *Gelidibacter algens* ATCC 700364 | 1 | 0.75 | *Lewinella cohaerens* ATCC 23123 | 2 | 9.89 |
| *Dyadobacter fermentans* ATCC 700827 | 2 | 0.33 | *Saprospira grandis* ATCC 23119 | 1 | 0.38 |

TABLE 1-continued

| Microbe | Reaction Time (hr) | Ala-Gln (mM) | Microbe | Reaction Time (hr) | Ala-Gln (mM) |
|---|---|---|---|---|---|
| *Flammeovirga aprica* NBRC 15941 | 1 | 0.16 | *Haliscomenobacter hydrossis* ATCC 27775 | 2 | 0.01 |

Example 2

Production of L-alanyl-L-glutamine from Various L-alanine Ester as Substrates

Microbial cells of *Pedobacter heparinus* NBRC 12017 were cultivated in the same manner as in Example 1 and recovered from the agar media. Recovered Microbial cells were suspended in a 0.1 M borate buffer (pH 9.0) containing 10 mM EDTA so as to prepare a suspension containing 100 g/l of wet microbial cells. 0.1 ml of the microbial cell suspension was admixed with 0.1 ml of 100 mM borate buffer (pH 9.0) containing 10 mM EDTA, 200 mM L-alanine ester hydrochloride described in Table 2 and 400 mM L-glutamine to prepare a total volume 0.2 ml of the reaction mixture, which was then subjected to the reaction at 20° C. for 1 hour. The amount (mM) of L-alanyl-L-glutamine (Ala-Gin) produced by each reaction is shown in Table 2.

TABLE 2

| Alanine ester | Ala-Gln (mM) |
|---|---|
| L-Alanine methyl ester hydrochloride | 29.52 |
| L-Alanine ethyl ester hydrochloride | 27.13 |
| L-Alanine isopropyl ester hydrochloride | 20.83 |
| L-Alanine-t-butyl ester hydrochloride | 2.65 |

INDUSTRIAL APPLICABILITY

The present invention is useful for producing dipeptides.

REFERENCES

JP-1-96194A
JP-6-234715A
JP-53-92729A
WO 90/01555
EP 278787A
Bull. Chem. Soc. Jpn., 34,739(1961)
Bull. Chem. Soc. Jpn., 35,1966(1962)
Bull. Chem. Soc. Jpn., 37,200(1964)
Biochemical J., 163, 531 (1977)

The invention claimed is:

1. A method for producing a dipeptide comprising:
reacting an amino acid ester with an N-non-protected amino acid to form the dipeptide in the presence of at least one member selected from the group consisting of a culture of a microbe, microbial cells separated from the culture, a treated microbial cell product, and a peptide-forming enzyme derived from the microbe,
wherein the microbe has an ability to form the dipeptide from the amino acid ester and the amino acid and belongs to a genus selected from the group consisting of *Cellulophaga lytica, Weeksella virosa, Pedobacter heparinus, Persicobacter diffluens, Flexithrix dorotheae, Chitinophaga pinensis, Cyclobacterium marinum, Runella slithyformis, Thermonema lapsum, Psychroserpens burtonensis, Gelidibacter algens, Dyadobacter fermentans, Flammeovirga aprica, Spirosoma linguale, Flectobacillus major, Tenacibaculum maritimum, Rhodothermus marinus, Zobellia galactanivorans, Muricauda ruestringensis, Salegentibacter salegens, Taxeobacter gelupurpurascens, Cytophaga hutchinsonii, Marinilahilia salmonicolor, Lewinella cohaerens, Saprospira grandis,* and *Haliscomenobacter hydrossis.*

2. The method according to claim 1, further comprising adding a metal enzyme inhibitor to a reaction mixture upon forming the dipeptide from the amino acid ester and the amino acid in the presence of at least one selected from the group consisting of the culture of the microbe, the microbial cells separated from the culture, the treated microbial cell product, and the peptide-forming enzyme derived from the microbe.

3. The method according to claim 1, wherein the amino acid ester is an L-alanine ester.

4. The method according to claim 1, wherein the amino acid is L-glutamine.

5. The method according to claim 1, wherein said reacting is in the presence of a culture of the microbe.

6. The method according to claim 5, wherein said amino acid ester and said amino acid are added directly to said culture.

7. The method according to claim 1, wherein said reacting is in the presence of microbial cells separated from a culture of the microbe.

8. The method according to claim 7, wherein said microbial cells are separated from said culture by centrifugation and said microbial cells are resuspended in a buffer solution, subsequently said amino acid ester and said amino acid are added directly to the resuspended microbial cells.

9. The method according to claim 1, wherein said reacting is in the presence of a treated microbial cell product.

10. The method according to claim 9, wherein said treated microbial cell product is selected from the group consisting of microbial cells disrupted by ultrasound, microbial cells disrupted by French press, microbial cells disrupted by glass beads, microbial cells lysed by egg white lysozyme, microbial cells lysed by peptidase treatment, dyno mill treated microbial cells, acetone-treated microbial cells, freeze-dried microbial cells or a combination of treatment methods thereof.

11. The method according to claim 10, wherein said treated microbial cells are partially purified to obtain a crude enzyme solution prior to reacting with said amino acid ester and said amino acid.

12. The method according to claim 1, wherein said reacting is in the presence of a peptide-forming enzyme derived from the microbe.

13. The method according to claim 1, wherein said amino acid ester is an ester of an L-amino acid, wherein said ester is selected from the group consisting of methyl esters, ethyl esters, n-propyl esters, isopropyl esters, n-butyl esters, isobutyl esters, and tert-butyl esters.

14. The method according to claim 1, wherein said amino acid ester is an ester of a D-amino acid, wherein said ester is selected from the group consisting of methyl esters, ethyl esters, n-propyl esters, isopropyl esters, n-butyl esters, isobutyl esters, and tert-butyl esters.

15. The method according to claim 1, wherein said amino acid ester is at a concentration ranging from 1 mM to 10M.

16. The method according to claim 1, wherein said amino acid is an L-amino acid.

17. The method according to claim 1, wherein said amino acid is a D-amino acid.

18. The method according to claim 1, wherein said amino acid is at a concentration ranging from 1 mM to 10M.

19. The method according to claim 1, wherein said reacting is at a temperature ranging from 3°C. to 70°C., a pH ranging from 2 to 12, and is conducted for a time ranging from 2 to 100 hours.

* * * * *